(12) United States Patent
Iaccino

(10) Patent No.: US 8,552,236 B2
(45) Date of Patent: Oct. 8, 2013

(54) PRODUCTION OF AROMATICS FROM METHANE

(75) Inventor: Larry L. Iaccino, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/887,634

(22) Filed: Sep. 22, 2010

(65) Prior Publication Data

US 2011/0077441 A1 Mar. 31, 2011

Related U.S. Application Data

(60) Provisional application No. 61/247,029, filed on Sep. 30, 2009.

(51) Int. Cl.
*C07C 2/76* (2006.01)

(52) U.S. Cl.
USPC ............ 585/418; 585/419; 585/420; 585/943

(58) Field of Classification Search
USPC .................. 585/418, 419, 420, 943
See application file for complete search history.

(56) References Cited

U.S. PATENT DOCUMENTS

| 3,140,253 | A | * | 7/1964 | Plank et al. ............. 208/120.15 |
| 3,244,643 | A | | 4/1966 | Schwartz |
| 3,843,741 | A | * | 10/1974 | Yan ................................. 585/407 |
| 4,727,206 | A | | 2/1988 | Clayson et al. |
| 5,026,937 | A | | 6/1991 | Bricker |
| 5,336,825 | A | | 8/1994 | Choudhary et al. |
| 6,239,057 | B1 | | 5/2001 | Ichikawa et al. |
| 6,426,442 | B1 | | 7/2002 | Ichikawa et al. |
| 6,784,333 | B2 | | 8/2004 | Juttu et al. |
| 6,811,684 | B2 | | 11/2004 | Mohr et al. |
| 7,179,764 | B2 | | 2/2007 | Basso et al. |
| 7,470,645 | B2 | | 12/2008 | Shan et al. |
| 7,754,930 | B2 | | 7/2010 | Iaccino |
| 7,781,636 | B2 | | 8/2010 | Iaccino et al. |
| 2005/0056568 | A1 | | 3/2005 | Bouchy et al. |
| 2006/0121239 | A1 | | 6/2006 | Furukawa et al. |
| 2007/0249880 | A1 | * | 10/2007 | Iaccino et al. ................ 585/418 |
| 2007/0260098 | A1 | | 11/2007 | Iaccino et al. |
| 2009/0029103 | A1 | | 1/2009 | Hiramatsu et al. |
| 2009/0275791 | A1 | | 11/2009 | Ercan |

FOREIGN PATENT DOCUMENTS

| DE | 102007031537 | 1/2009 |
| EP | 0 228 267 | 7/1987 |
| EP | 1 222 961 | 7/2002 |
| WO | 2009/034268 | 3/2009 |
| WO | 2009/097067 | 8/2009 |

OTHER PUBLICATIONS

Gu et al., "Template-Synthesized Porous Silicon Carbide as an Effective Host for Zeolite Catalysts", Chem. Eur. J. 2009, 15, pp. 13449-13455.

* cited by examiner

*Primary Examiner* — Thuan D Dang
(74) *Attorney, Agent, or Firm* — Andrew B. Griffis

(57) ABSTRACT

A catalyst for the conversion of methane to higher hydrocarbons including aromatic hydrocarbons comprises particles of a porous refractory material, crystals of a zeolite material grown within the pores of the refractory material, and at least one catalytically active metal or metal compound associated with the zeolite crystals.

17 Claims, No Drawings

PRODUCTION OF AROMATICS FROM METHANE

CROSS REFERENCE TO RELATED APPLICATIONS

This application claims the benefit of Provisional Application No. 61/247,029, filed Sep. 30, 2009, the disclosure of which is incorporated by reference in its entirety.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal supported on a zeolite, such as ZSM-5, at high temperature, such as 600° C. to 1000° C.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mol % hydrogen and 50 mol % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

Further in our U.S. Published Patent Application No. 2007/0260098, we have described a process for converting methane to higher hydrocarbons including aromatic hydrocarbons, the process comprising contacting a feed containing methane with a dehydrocyclization catalyst, conveniently molybdenum, tungsten and/or rhenium or a compound thereof on ZSM-5 or an aluminum oxide, under conditions effective to convert said methane to aromatic hydrocarbons and produce a first effluent stream comprising aromatic hydrocarbons and hydrogen, wherein said first effluent stream comprises at least 5 wt % more aromatic rings than said feed; and reacting at least part of the hydrogen from said first effluent stream with an oxygen-containing species to produce a second effluent stream having a reduced hydrogen content compared with said first effluent stream.

Despite these proposals, the successful application of reductive coupling to produce aromatics on a commercial scale requires the solution of a number of serious technical challenges. For example, the reductive coupling process is both endothermic and thermodynamically limited. Thus the reaction is generally conducted at high temperatures, such as in excess of 700° C., but the cooling effect caused by the reaction lowers the reaction temperature sufficiently to greatly reduce the reaction rate and total thermodynamic conversion if significant make-up heat is not provided to the process. In addition, the process tends to produce carbon and other non-volatile materials, collectively referred to as "coke", that accumulate on the catalyst resulting in reduced activity and potentially undesirable selectivity shifts, as well as loss of valuable feedstock. The inventor has therefore now concluded that, in an embodiment, the process is best operated in a moving or fluidized bed reaction system which also allows for rapid and repeated transfer of the catalyst between a reaction cycle and a regeneration cycle as well as enabling heat supply by means of hot solids carrying heat into the reactor.

As a result of consideration of these and other constraints on the reductive coupling reaction, the inventor has also now determined that in embodiments the optimum catalyst employed must meet an exacting specification including some or all of the following properties:

(a) high hardness to resist mechanical attrition;
(b) high mechanical strength to resist attrition due to thermal shock;
(c) high thermal conductivity to reduce aging during reheating;
(d) high heat capacity to reduce the catalysts circulation rate required to provide a given heat input to the system;
(e) high particle density to allow higher gas velocities in the reactor;
(f) absence of components that directly or indirectly promote coke formation; and
(g) high accessibility to catalytically active sites to provide improved resistance to catalyst deactivation by coke accumulation.

In view of these constraints, there is a continuing need to find new catalyst systems that are tailored to the exacting duty required by the reductive coupling reaction.

In accordance to the invention, it has now been found that an improved catalyst for the dehydroaromatization of methane can be produced by using, as a catalyst support, zeolite crystals grown in the pores of a porous refractory material, such as foamed silicon carbide, and depositing the catalytically active component(s) on the zeolite.

U.S. Pat. No. 7,179,764 discloses a catalyst composite comprising a zeolite deposited on a support, wherein the support comprises silicon carbide (SiC) with a specific BET surface area of at least 5 m$^2$/g, wherein the support comprises a silicon carbide foam. However, the catalyst composite is produced by creating a surface layer of silica between 1 and 10 nm thick measured by XPS on the support by calcination; putting the support in contact with a previously set gel that is capable of forming the zeolite, and conducting a hydrothermal synthesis to form the zeolite.

U.S. Published Patent Application No. 2005/0056568 discloses the use of supported catalysts comprising at least one metal or metallic compound of a metal from group VI and/or group VIII deposited on a support essentially constituted by β-silicon carbide in a process for selective hydrodesulphurization of an olefinic hydrocarbon feed that is substantially free of polynuclear aromatics and metals. The process is said to allow deep desulphurization of catalytically cracked gasoline cuts with very limited saturation of olefins and thus a minimum loss of octane number.

U.S. Published Patent Application No. 2006/0121239, the entire disclosure of which is incorporated herein by reference, discloses a silicon carbide based porous material containing silicon carbide particles as an aggregate and metallic silicon as a bonding material and having a number of pores formed by them, characterized in that it has an oxide phase in at least a part of the pores, and the oxide phase contains respective oxides of silicon, aluminum and an alkaline earth metal and contains substantially no alkaline earth metal silicate crystal phase.

U.S. Published Patent Application No. 2009/0029103, the entire disclosure of which is incorporated herein by reference, discloses a silicon carbide-based porous article comprising silicon carbide particles as an aggregate, metallic silicon and an aggregate derived from siliceous inorganic particles to form pores through volume shrinkage by heat treatment, wherein the porosity is 45 to 70%, and the average pore diameter is 10 to 20 μm. The article is produced by a method comprising; adding inorganic particles to form pores through volume shrinkage by heat treatment to a raw-material mixture containing silicon carbide particles and metallic silicon, then forming into an intended shape, calcinating and firing the resultant green body, forming pores through volume shrinkage of the inorganic particles by heat treatment, and the shrunk inorganic particles being present as an aggregate in the porous article.

International Patent Publication No. WO2009/034268, the entire disclosure of which is incorporated herein by reference, discloses a composite, useful as a catalyst substrate, comprising a layer of porous alumina deposited on a rigid substrate made of beta-SiC. The alumina layer may include catalytically active phases, in particular phases that do not properly bind onto the non-treated beta-SiC, such as silver particles.

German Patent Publication No. 102007031537, the entire disclosure of which is incorporated herein by reference, discloses a process for producing a porous silicon carbide composite having active functional centers. The process comprises forming a microemulsion containing a chemical compound or element for formation of the active functional center, a non ionic surfactant and an organic silicon-containing compound. The microemulsion is subjected to thermal treatment at 1100-1500° C. in an inert atmosphere to a form of silicon carbide containing functional centers and the residual carbon is removed by heating in an oxidizing atmosphere at 1000° C.

SUMMARY

In one aspect, the invention resides in a catalyst for the conversion of methane to higher hydrocarbons including aromatic hydrocarbons, the catalyst comprising particles of a porous refractory material, crystals of a zeolite material grown within the pores of the refractory material, and at least one catalytically active metal or metal compound associated with the zeolite crystals.

Conveniently, the porous refractory material has a porosity of at least 20%, such as at least 30%, for example at least 40%, typically at least 50%.

Conveniently, at least 50%, and typically at least 90%, of the pore volume of the pores of the porous refractory material have a diameter in excess of 5 nm.

Conveniently, the particles of the porous refractory material are spherical and have an average diameter between about 50 and about 5000 μm.

Conveniently, the catalyst has a particle density between about 1.1 and about 3.5 gm/cc.

Conveniently, the porous refractory material has a Davison Index less than 1.0, such as less than 0.5 and for example less than 0.2; a bulk crush strength greater than 5 MPa, such as greater than 10 MPa and for example greater than 20 MPa; a thermal conductivity of at least 3 W/(m° C.) and a heat capacity (measured at 800° C.) of at least 0.8 J/(g° C.), such as at least 1.0 J/(g° C.) and for example at least 1.2 J/(g° C.).

Conveniently, the porous refractory material is selected from silicon carbide, zirconia, ceria, yttria, alumina, silica, titania, or combinations thereof. In one embodiment, the porous refractory material comprises a silicon carbide foam.

Conveniently, the zeolite material is selected from framework types MFI, MEL, MTW, TON, MTT, FER, MFS, MWW, IWR, KFI, BEA, ITH, MOR, FAU, LTL, IWW, VFI and mixtures thereof.

Conveniently, the crystals of zeolite material have an average particle size of less than 2 nm; such as less than 1.0 nm; for example between 0.2 and 0.8 nm.

Conveniently, said at least one catalytically active metal is selected from molybdenum, tungsten, rhenium, and niobium.

In a further aspect, the invention resides in a process for converting methane to higher hydrocarbons including aromatic hydrocarbons, the process comprising contacting a feed comprising methane with a dehydrocyclization catalyst in a reaction zone under conditions effective to convert said methane to aromatic hydrocarbons, said dehydrocyclization catalyst comprising particles of a porous refractory material, crystals of a zeolite material grown within the pores of the refractory material, and at least one catalytically active metal or metal compound associated with the zeolite crystals.

DETAILED DESCRIPTION

As used herein the term "higher hydrocarbon(s)" means hydrocarbon(s) having more than one carbon atom per molecule, e.g., ethane, ethylene, propane, propylene, benzene, toluene, xylenes, naphthalene, and/or methyl naphthalene.

As used herein the term "aromatic hydrocarbon(s)" means molecules containing one or more aromatic rings. Examples of aromatic hydrocarbons are benzene, toluene, xylenes, naphthalene, and methylnaphthalenes.

The terms "coke" and "carbonaceous material" are used herein interchangeably to mean carbon containing materials, which are essentially non-volatile solids at the reaction conditions, with a low hydrogen content relative to carbon content (such as a H/C molar ratio of less than 0.8; most probably less than 0.5). These may include crystalline graphite, graphitic sheets, graphitic fragments, amorphous carbon, or other carbon containing structures which are essentially non-volatile solids at the reaction conditions.

The present invention provides a catalyst and process for the conversion of methane to higher hydrocarbons including aromatic hydrocarbons. The catalyst comprising particles of a porous refractory material, such as silicon carbide, crystals of a zeolite material grown within the pores of the refractory material, and at least one catalytically active metal or metal compound associated with the zeolite crystals. As will be discussed in more detail below, the process generally comprises contacting a methane-containing feed in a substantially countercurrent fashion with one or more fluidized or moving beds of the dehydrocyclization catalyst.

The conversion of methane to aromatics generates hydrogen as a by-product and hence the present process also includes one or more hydrogen utilization steps in which at least part of the hydrogen by-product is converted to higher value products.

Feedstock

Any methane-containing feedstock can be used in the present process but in general the process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can be converted directly to aromatics products in the dehydrocyclization step. In addition, as will be discussed below, carbon dioxide can be converted to useful aromatics products either directly in the dehydrocyclization step or indirectly through conversion to methane and/or ethane in a hydrogen utilization step.

Nitrogen and/or sulfur impurities are also typically present in methane-containing streams and desirably are removed, or reduced to low levels, prior to use of the streams in the present process. In an embodiment, the feed to the dehydrocyclization step contains less than 100 ppm, for example less than 10 ppm, such as less than 1 ppm each of nitrogen and sulfur compounds.

In addition, the feed to the dehydrocyclization step may contain at least one of hydrogen, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from a hydrogen utilization step, added as separate co-feeds or can be present in the methane stream, such as, for example, when ethane is present in a natural gas feed. Higher hydrocarbons recycled from a hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3+$ hydrocarbons.

Dehydrocyclization Catalyst

The dehydrocyclization catalyst employed herein comprises a particulate support composed of a refractory material, such as silicon carbide, zirconia, ceria, yttria, alumina, silica, titania, or combinations thereof. The particles of the support are porous, typically with a porosity of at least 20%, such as at least 30%, for example at least 40%, generally at least 50%. In addition, the porosity of the support is typically arranged so that at least 50%, typically at least 90%, of the pore volume of the pores of the porous refractory material have a diameter in excess of 5 nm.

Generally, in preferred embodiments, the particulate support has one or more of the following physical properties:

(a) a high hardness so as to resist mechanical attrition as evidenced by a Davison Index less than 1.0, preferably less than 0.5, more preferably less than 0.2. The Davison Index (DI) is determined as follows: a 7.0 g sample of the support is screened to remove particles in the 0 to 20 micron size range. The particles above 20 microns are then subjected to a 1 hour test in a standard Roller Particle Size Analyzer using a hardened steel jet cup having a precision bored orifice. An air flow of 21 liters/minute is used. The Davison Index is calculated as follows:

$$DI = \frac{\text{wt. \% 0-20 micron material formed during the test}}{\text{wt. original 20+ micron fraction}}$$

(b) a high mechanical strength to resist attrition due to thermal shock as evidenced by a bulk crush strength greater than 5 MPa; preferably greater than 10 MPa; more preferably greater than 20 MPa;

(c) a thermal conductivity of at least 3 W/(m° C.);

(d) a heat capacity (measured at 800° C.) of at least 0.8 J/(g° C.), preferably at least 1.0 J/(g° C.), more preferably at least 1.2 J/(g° C.).

In one embodiment, the porous refractory material comprises a silicon carbide foam.

Generally, the particles of the porous refractory material are spherical and have an average diameter between about 50 and about 5000 μm, such as between about 100 and about 500 μm, generally about 300 μm.

In addition, the catalyst comprises crystals of a zeolite material grown within the pores of the refractory material. Since the zeolite is located within the pores of the refractory material, the crystal size of the zeolite is preferably small, typically the average particle size being less than 2 nm; such as less than 1.0 nm; for example between 0.2 and 0.8 nm.

Suitable aluminosilicate zeolites for use in the present dehydrocyclization catalyst include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), and VFI (e.g., VPI-5), as well as materials such as MCM-68, EMM-1, EMM-2, ITQ-23, ITQ-24, ITQ-25, ITQ-26, ETS-2, ETS-10, SAPO-17, SAPO-34 and SAPO-35.

Generally, the aluminosilicate zeolite employed herein has a Constraint Index between about 1 and about 12 (as defined in U.S. Pat. No. 4,016,218, which is incorporated herein by reference) and typically is ZSM-5. Conveniently, the aluminosilicate zeolite has a silica to alumina mole ratio between about 14 and about 500, such as between about 20 and about 300, for example between about 22 and about 280.

Growing the zeolite crystals in the pores of the refractory material can be effected by any method known in the art. Typically, however, the particles of the refractory material are treated with an aqueous mixture capable of forming the desired zeolite and the treated particles are then heated at a temperature from about 30° C. to about 300° C. for about 1 hour to 10 days to allow crystals of the zeolite to form.

The as-synthesized zeolite can be modified by known methods, such as, for example, calcining to remove any organic directed agent used to facilitate the synthesis, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the zeolite and hinder or enhance access to the internal pore structure of the zeolite.

Associated on the zeolite crystals, and more particularly deposited in the pores of the zeolite crystals, is at least one catalytically active metal or metal compound, which is generally selected from molybdenum, tungsten, rhenium, and niobium. Conveniently, the catalytically active metal or metal compound is present in an amount between about 0.1% and about 20%, such as between about 0.5% and about 10%, for example between 1% and 8%, based on elemental metal by weight of the total catalyst. A preferred metal is molybdenum. Catalyst modifiers may also be deposited in the zeolites pores in addition to the main catalytically active metal(s), suitable modifiers including gallium, iron, cobalt and mixtures and compounds thereof.

Typically the catalyst particles have a particle density between about 1.1 and about 3.5 gm/cc.

Dehydrocyclization Process

In the dehydrocyclization step of the present process, the methane containing feedstock is contacted with the particulate dehydrocyclization catalyst under conditions, normally non-oxidizing conditions and typically reducing conditions, effective to convert the methane to higher hydrocarbons, including benzene and naphthalene. The principal net reactions involved are as follows:

$$2CH_4 \leftrightarrow C_2H_4 + 2H_2 \quad \text{(Reaction 1)}$$

$$6CH_4 \leftrightarrow C_6H_6 + 9H_2 \quad \text{(Reaction 2)}$$

$$10CH_4 \leftrightarrow C_{10}H_8 + 16H_2 \quad \text{(Reaction 3)}$$

Carbon dioxide that may be present in the feed improves catalyst activity and stability by facilitating reactions such as:

$$CO_2 + \text{coke} \rightarrow 2CO \quad \text{(Reaction 4)}$$

but negatively impacts equilibrium by allowing competing net reactions, such as:

$$CO_2 + CH_4 \leftrightarrow 2CO + 2H_2 \quad \text{(Reaction 5).}$$

The dehydrocyclization step is conducted by contacting the methane-containing feedstock with the particulate dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction.

In some embodiments, a non-catalytic particulate material may be supplied to the dehydrocyclization reaction zone(s) in addition to the catalytic particulate material. The non-catalytic particulate material may be used as a material to transport energy (heat) into the system and/or to fill space as required providing the required hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide.

Typically, the mass ratio of the flowrate of the catalytic particulate material plus any non-catalytic particulate material over the flowrate of the hydrocarbon feedstock in the or each dehydrocyclization reaction zone is from about 1:1 to about 100:1, such as from about 1:1 to about 40:1, for example from about 5:1 to 20:1.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence, in some configurations, the difference between the maximum and minimum temperatures can be reduced to essentially zero. Alternatively, by supplying heated catalyst to the dehydrocyclization reaction, it is possible to produce an inverse temperature profile; that is with the process gas outlet reaction temperature being greater than the process gas inlet reaction temperature.

In one embodiment, the countercurrent flow of the feedstock and the particulate dehydrocyclization catalyst is arranged to produce an inverse temperature profile across dehydrocyclization reaction system, such that, despite the endothermic nature of the dehydrocyclization reaction, the difference between the reaction temperature of the gaseous effluent at the outlet from the dehydrocyclization reaction system and the reaction temperature of the methane-containing feed at the inlet to the dehydrocyclization reaction system is at least +10° C., such as at least +50° C., for example at least +100° C., and even at least +150° C.

Examples of suitable reactor designs for the dehydrocyclization step are disclosed in U.S. Published Patent Application Nos. 2007/0129587, 2007/0249879, 2007/0249880, 2007/0276171 and 2007/0293709, the entire disclosures of which are incorporated herein by reference.

In any event, since the dehydrocyclization reaction is endothermic, the catalytic particulate material enters the dehydrocyclization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C.

Other conditions used in the dehydrocyclization reaction generally include a pressure of about 1 kPa to about 1000 kPa, such as about 10 to about 500 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^{-1}$. Conveniently, the dehydrocyclization step is conducted in the absence of $O_2$.

Catalyst Regeneration

The dehydrocyclization reaction tends to deposit coke on the catalyst and hence, to maintain the activity of the catalyst, at least part of the catalyst is continuously or intermittently regenerated. This is typically achieved by withdrawing a portion of the catalyst from the or each reaction zone, either on an intermittent, or a continuous basis, and then transferring the catalyst portion to a separate regeneration zone. In the regeneration zone, the coked dehydrocyclization catalyst is contacted with a regeneration gas under conditions effective to remove at least a portion of the carbonaceous material on the catalyst. The regeneration zone may be a reactor operated as a fluidized bed, an ebulating bed, a settling bed, a riser reactor or a combination thereof. In practice, each regeneration zone may include a plurality of reactors, such as a plurality of riser reactors connected in parallel or a plurality of reactors connected in series such as a riser reactor followed by a settling bed. After regeneration the catalyst is returned to reaction zone.

In one embodiment, the regeneration is conducted in the presence of an oxygen-containing gas. Generally, the oxygen-containing gas contains less $O_2$ than air, such as less than 10 wt %, more preferably less than 5 wt %, $O_2$, and is preferably substantially free of $H_2O$. The regeneration gas may also contain $CO_2$ to gasify a portion of the coke from the catalyst. Convenient sources of the regeneration gas are an $O_2$ depleted, $N_2$ enriched stream from an air separation unit and a high $CO_2$ reject stream from industrial or natural gas processing to which air or $O_2$ has been added to achieve the target $O_2$ concentration. Suitable conditions for regeneration with an oxygen-containing gas include a temperature from about 400° C. to about 700° C., such as from about 550° C. to about 650° C., a pressure between 10 and 100 psia (69 and 690 kPa), such as between 15 and 60 psia (103 and 414 kPa), and a catalyst residence time between 0.1 and 100 minutes, such as between 1 and 20 minutes.

Alternatively, the regeneration can be conducted in the presence of a hydrogen-containing gas whereby coke on the catalyst is converted to methane. Generally, the hydrogen-containing gas should not contain significant quantities of methane or other hydrocarbons; typically with the hydrocarbon content being less than 20 mol %, such as less than 10 mol %, for example less than 2 mol %. In one embodiment, the hydrogen required for the regeneration is obtained at least in part from the hydrogen-containing effluent from the dehydrocyclization reaction. Conveniently, hydrogen regeneration conditions comprise a temperature from about 700° C. to about 1200° C., such as from about 800° C. to about 1000° C., such as about 850° C. to about 950° C. and a pressure of at least 100 kPaa, such between about 150 kPaa and about 5000 kPaa.

Generally, the coked dehydrocyclization catalyst removed from the or each reaction zone will be at a lower temperature than the optimum for hydrogen regeneration and hence the removed catalyst is initially heated to the desired regeneration temperature by direct and/or indirect contact with combustion gases produced by combustion of a supplemental source of fuel. The heating is conducted in a heating zone which may be in the same vessel as the regeneration zone or which may be in a separate vessel from the regeneration zone. By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, in the case of direct heat transfer to the dehydrocyclization catalyst, the use of an oxygen-lean atmosphere minimizes oxidation of metal carbides present in the catalyst and reduces the average steam partial pressure and hence hydrothermal catalyst aging.

Alternatively, a suitable supplemental fuel source is hydrogen and, in particular, part of the hydrogen generated as a by-product of the aromatization reaction.

Examples of suitable designs for the regeneration step are disclosed in U.S. Published Patent Application Nos. 2007/0249740 and 2008/0249342, the entire disclosures of which are incorporated herein by reference.

Catalyst Reheating

Since the dehydrocyclization reaction is endothermic, it is necessary to supply heat to the reaction. In the present process, this is conveniently achieved by withdrawing part of the catalyst from the reaction zone, either on an intermittent or a continuous basis, and transferring it to a separate heating zone, where the catalyst is heated by direct or indirect contact with hot combustion gases generated by burning a supplemental source of fuel. The heated catalyst is then returned to the reaction zone. Examples of suitable designs for the catalyst reheating step are disclosed in U.S. Published Patent Application Nos. 2007/0129587 and 2008/0276171, the entire disclosures of which are incorporated herein by reference.

Where catalyst regeneration is effected in the presence of hydrogen, the preheating of the coked catalyst normally required to bring the catalyst to the optimum regeneration temperature may provide one possible route for supplying heat to the dehydrocyclization reaction. Similarly, oxidative regeneration is highly exothermic and can also be used to supply heat. However, to maintain heat balance using regeneration as the sole source of heat to the reaction, the process requires a high selectivity to coke rather than to the desired aromatic products. Thus, even, with oxidative regeneration, it will generally be desirable to employ a separate catalyst reheating step in addition to a catalyst regeneration step. Details of a method and apparatus for providing separate catalyst reheating and regeneration in the production of aromatics from methane can be found in U.S. Published Patent Application No. 2007/0249740 mentioned above.

Catalyst Recarburizing

It will be appreciated that heating the dehydrocyclization catalyst for the purposes of regeneration and/or for heat transfer may subject the catalyst to oxidizing conditions, especially where catalyst heating involves direct contact with hot combustion gases. As a result, metals, such as rhenium, tungsten or molybdenum, present in the dehydrocyclization catalyst may be converted during the heating step from their catalytically active elemental or carbide form to an oxide species. Thus, before being returned to the reaction zone, the regenerated and/or reheated catalyst may be transferred to a catalyst treatment zone separate from the regeneration zone, the heating zone and the reaction zone, where the catalyst is contacted with a carburizing gas containing at least one hydrocarbon selected from methane, ethane, propane, butane, isobutene, hexane, benzene and naphthalene. In some cases, the carburizing gas may also contain at least one of $CO_2$, CO, $H_2$, $H_2O$ and inert diluents. Alternatively, the carburizing gas may be a mixture of hydrogen and at least one of CO and $CO_2$. Moreover, it may be desirable to contact the catalyst sequentially with a plurality of different carburizing gases, each comprising a hydrocarbon selected from methane, ethane, propane, butane, isobutene, hexane, benzene and naphthalene or a mixture of hydrogen and at least one of CO and $CO_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in the regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psia (69 and 690 kPa), such as between 15 and 60 psia (103 and 414 kPa). Generally, the average residence time of catalyst particles in the catalyst treatment zone will be between 0.1 and 100 minutes, for example, between 1 and 20 minutes. Under these conditions, the carburizing gas reacts with metal oxide species on the catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can be supplied to the catalyst and/or the carburizing gas prior to or during the carburization step. For example heat can be supplied to the catalyst by indirect heating, by contacting with hot flue gas from the reaction zone or the heating zone, by contacting with the hot gaseous effluent from the carburization process, or by mixing with heated catalyst from the heating zone. Heat is conveniently supplied to the carburization gas by means of an external furnace or heat exchanger or by with heated catalyst from the heating zone.

In some cases, it may be desirable that the heated unregenerated catalyst is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

In practice, as the dehydrocyclization reaction proceeds, fresh dehydrocyclization catalyst will be added to the process either to make up for catalyst lost by mechanical attrition or deactivation and, although there are multiple means of the addition of fresh catalyst, to avoid damage to the catalyst, it is generally desirable to add fresh catalyst to a region of the process that is operating at a temperature below the maximum temperature in each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another embodiment, the catalyst may be added to the lower temperature regions of a reactor system with an inverse temperature profile.

Product Separation and Hydrogen Management

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt %, conveniently at least 30 wt %, more aromatic rings than the feed.

The benzene and naphthalene are separated from the dehydrocyclization effluent, for example, by solvent extraction followed by fractionation, and can be recovered as a product stream. The aromatic product can be marketed as-is or, at least part of the aromatic product can be submitted to an alkylation step, before or after product recovery, to produce higher value materials, such as xylenes. In addition, the present process utilizes the hydrogen generated as a by-product of the dehydrocyclization reaction and in particular converts at least part of the hydrogen to higher value products.

Typically, hydrogen utilization comprises at least one of the following:

(i) reaction with carbon dioxide to produce methane and/or ethane, can be recycled directly to the dehydrocyclization step to generate additional aromatic products;

(ii) reaction with carbon monoxide according to the Fischer-Tropsch process to produce $C_2$ to $C_5$ paraffins and olefins, which can be recovered as products or recycled back to the dehydrocyclization step;

(iii) reaction with carbon monoxide to produce $C_1$ to $C_3$ alcohols, and particularly methanol, which can be used to alkylate the aromatics generated in the dehydrocyclization step to higher value products, such as xylenes, or can be used as a feedstock for the production of lower olefins, particularly ethylene and propylene; and (iv) selective combustion of the hydrogen in a mixed stream containing hydrocarbons to form water or steam without substantially reacting hydrocarbons in the stream with oxygen to form carbon monoxide, carbon dioxide, and/or oxygenated hydrocarbons.

The above processes steps may be employed sequentially to gain the greatest benefit; for example Fischer-Tropsch may first be employed to yield a $C_2$+ enriched stream followed by methanation to achieve high conversion of the $H_2$.

A detailed discussion of these hydrogen utilization processes can be found in U.S. Published Patent Application No. 2007/0260098, the entire contents of which are incorporated herein by reference.

It will be appreciated that aromatic hydrocarbons, like all hydrocarbons, inherently contain deuterium and $^{13}C$ in amounts that can vary according to the source of the carbon and hydrogen atoms in the molecule. In particular, studies of isotope distributions have shown that the amounts of deuterium and $^{13}C$ in naturally-occurring geologic methane are significantly different from the amounts of deuterium and $^{13}C$ in naphtha and that the amount of $^{13}C$ in naturally-occurring geologic $CO_2$ is significantly different from the amounts of $^{13}C$ in naturally-occurring geologic methane and in naphtha. Thus, analysis of the distribution of deuterium and $^{13}C$, can be used to differentiate between aromatic hydrocarbons produced using the present dehydrocyclization process and aromatic hydrocarbons produced from naphtha.

Thus, for example, if the measure of isotope abundance for deuterium in a benzene or xylene sample is defined as:

$$\delta(\text{deuterium}) = (R'_{sample}/R'_{standard} - 1) \times 1000$$

where $R'_{sample}$ is the ratio of deuterium to hydrogen in the benzene or xylene; and $R'_{standard}$ is the ratio of the natural abundance of deuterium to the natural abundance of hydrogen (which is equal to 0.00015/0.99985); and the measure of isotope abundance for $^{13}C$ in the sample is defined as:

$$\delta(^{13}C) = (R''_{sample}/R''_{standard} - 1) \times 1000$$

where $R''_{sample}$ is the ratio of $^{13}C$ to $^{12}C$ in the benzene or xylene; and $R''_{standard}$ is the ratio of the natural abundance of $^{13}C$ to the natural abundance of $^{12}C$ (which is equal to 0.01109/0.98891), then the following apply:

Benzene produced according to the present process comprises deuterium and $^{13}C$ in amounts such that δ(deuterium) for the benzene is less than −250, preferably greater than −450 and less than −250, and $\delta(^{13}C)$ for the benzene is less than −24, preferably greater than −59 and less than −24.

Xylene produced according to the present process comprises deuterium and $^{13}C$ in amounts such that the δ(deuterium) value is less than −250, preferably greater than −450 and less than −250, and the $\delta(^{13}C)$ value is less than −24, preferably greater than −60 and less than −24.

A detailed discussion of these methods of isotope distribution can be found in U.S. Published Patent Application No. 2007/282145, the entire contents of which are incorporated herein by reference While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for converting methane to higher hydrocarbons including aromatic hydrocarbons, the process comprising contacting a feed comprising methane and hydrogen gas and less than 5 wt. % C3+ hydrocarbons with a dehydrocyclization catalyst in a reaction zone under conditions effective to convert said methane to aromatic hydrocarbons, wherein said dehydrocyclization catalyst enters said reaction zone at a temperature of about 900-1100° C., said dehydrocyclization catalyst comprising particles of a porous refractory material, crystals of a zeolite material grown within the pores of the refractory material, and a catalytically active metal or metal compound of molybdenum associated with the zeolite crystals, said process further comprising a step of catalyst regeneration followed by a step of catalyst recarburization in a catalyst treatment zone separate from said reaction zone.

2. The process of claim 1, wherein the porous refractory material has a porosity of at least 20%.

3. The process of claim 1, wherein at least 50% of the pore volume of the pores of the porous refractory material have a diameter in excess of 5 nm.

4. The process of claim 1, wherein at least 90% of the pore volume of the pores of the porous refractory material have a diameter in excess of 5 nm.

5. The process of claim 1, wherein the particles of the porous refractory material are spherical and have an average diameter between about 50 and about 5000 μm.

6. The process of claim 1, wherein the catalyst has a particle density between about 1.1 and about 3.5 gm/cc.

7. The process of claim 1, wherein the porous refractory material has a Davison Index less than 1.0.

8. The process of claim 1, wherein the porous refractory material has a bulk crush strength greater than 5 MPa.

9. The process of claim 1, wherein the porous refractory material has a thermal conductivity of at least 3 W/(m° C.).

10. The process of claim 1, wherein the porous refractory material has a heat capacity (measured at 800° C.) of at least 0.8 J/(g° C.).

11. The process of claim 1, wherein the porous refractory material is selected from silicon carbide, zirconia, ceria, yttria, alumina, silica, titania, or combinations thereof.

12. The process of claim 1, wherein the porous refractory material comprises a silicon carbide foam.

13. The process of claim 1, wherein the zeolite material is selected from framework types MFI, MEL, MTW, TON, MTT, FER, MFS, MWW, IWR, KFI, BEA, ITH, MOR, FAU, LTL, IWW, VFI and mixtures thereof.

14. The process of claim 1, wherein the crystals of zeolite material have an average particle size of less than 2 nm.

15. The process of claim 1, further including a catalyst modifier different from said catalytically active metal or metal compound and also associated on the zeolite crystals.

16. The process of claim 15, wherein the catalyst modifier is selected from gallium, iron, cobalt and mixtures and compounds thereof.

17. The process of claim 1, wherein the porous refractory material comprises a silicon carbide foam and there is a catalyst modifier selected from gallium, iron, cobalt and mixtures and compounds thereof.

* * * * *